(12) United States Patent
Salviato et al.

(10) Patent No.: US 10,416,053 B2
(45) Date of Patent: Sep. 17, 2019

(54) GRIPS FOR A LINEAR FRACTURE TESTING MACHINE AND METHOD OF DESIGNING SAME

(71) Applicant: Northwestern University, Evanston, IL (US)

(72) Inventors: Marco Salviato, Seattle, WA (US); Viet T. Chau, Chicago, IL (US); Weixin Li, Evanston, IL (US); Zdeněk P Bažant, Evanston, IL (US); Gianluca Cusatis, Wilmette, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

(21) Appl. No.: 15/877,932

(22) Filed: Jan. 23, 2018

(65) Prior Publication Data

US 2018/0259431 A1    Sep. 13, 2018

Related U.S. Application Data

(60) Provisional application No. 62/449,167, filed on Jan. 23, 2017.

(51) Int. Cl.
*G01N 1/00* (2006.01)
*G01N 1/36* (2006.01)
(Continued)

(52) U.S. Cl.
CPC ............... *G01N 1/36* (2013.01); *G01N 3/04* (2013.01); *G01N 3/405* (2013.01);
(Continued)

(58) Field of Classification Search
CPC ........... G01N 1/36; G01N 3/04; G01N 3/405; G01N 2001/364; G01N 2203/0017; G01N 2203/0278
(Continued)

(56) References Cited

U.S. PATENT DOCUMENTS 3,724,266 A * 4/1973 Beckstrom ............... G01N 3/08
                                                                73/808
4,478,086 A * 10/1984 Gram ....................... G01N 3/08
                                                                73/781

(Continued)

OTHER PUBLICATIONS

Tsai, S.W. et al., A General Theory of Strength for Anisotropic Materials, J. Composite Materials, vol. 5, pp. 58-80 (1971).

(Continued)

*Primary Examiner* — Max H Noori
(74) *Attorney, Agent, or Firm* — Benesch, Friedlander, Coplan & Aronoff LLP

(57) ABSTRACT

Test fixture grips for testing quasibrittle materials, such as fiber-polymer composites are provided having increased mass and stiffness relative to standard test grips to provide for obtaining postpeak measurements. The design is based on static analysis (using the second law of thermodynamics), confirmed by dynamic analysis of the test setup as an open system. Dynamic analysis of the test setup as a closed system with PID controlled input further indicates that the controllability of postpeak softening under CMOD control is improved not only by increasing the grip stiffness but also by increasing the grip mass.

15 Claims, 12 Drawing Sheets

(51) Int. Cl.
  *G01N 3/40* (2006.01)
  *G01N 3/04* (2006.01)
(52) U.S. Cl.
  CPC .............. *G01N 2001/364* (2013.01); *G01N 2203/0017* (2013.01); *G01N 2203/0278* (2013.01)
(58) Field of Classification Search
  USPC .......................................................... 73/833
  See application file for complete search history.

(56) References Cited

U.S. PATENT DOCUMENTS

| | | | | |
|---|---|---|---|---|
| 5,178,017 | A * | 1/1993 | Dinzburg | G01N 3/20 73/849 |
| 7,770,467 | B1 * | 8/2010 | Halderman | G01N 3/04 73/849 |
| 2007/0227259 | A1 * | 10/2007 | Alba | G01N 3/16 73/831 |
| 2009/0301216 | A1 * | 12/2009 | Sykes | G01N 3/00 73/833 |
| 2010/0000329 | A1 * | 1/2010 | Lorenz | G01N 3/04 73/856 |
| 2010/0229652 | A1 * | 9/2010 | Jeppesen | G01N 3/08 73/856 |
| 2013/0192384 | A1 * | 8/2013 | Chang | G01N 3/18 73/834 |

OTHER PUBLICATIONS

Hinton, M.J. et al., Predicting Failure in Composite Laminates: The Background to the Exercise, Composites Science and Technology 58, pp. 1001-1010 (1998).
Soden, P.D. et al., A Comparison of the Predictive Capabilities of Current Failure Theories for Composite Laminates, Composites Science and Technology 58, pp. 1225-1254, (1998).
Hinton, M. J. et al., A comparison of the predictive capabilities of current failure theories for composite laminates, judged against experimental evidence, Composites Science and Technology 62, pp. 1725-1797 (2002).
Bažant, Z.P., Size Effect in Blunt Fracture: Concrete, Rock, Metal, Journal of Engineering Mechanics, ASCE, vol. 110, No. 4, 518-535, (1984).
Bažant, Z.P. et al., Stability of Structures: Elastic, Inelastic, Fracture and Damage Theories, Oxford University Press, New York (1991) (also 2nd. ed. Dover Publ. 2003, 3rd ed. World Scientific 2010).
Bažant, Z.P. et al., Fracture and Size Effect in Concrete and Other Quasibrittle Material, CRC Press, Boca Raton and London (1998).
Bažant, Z.P. et al., Size Effect and Fracture Characteristics of Composite Laminates, Journal of Engineering Materials and Technology, vol. 118, pp. 317-324, (1996).
Green, B.G. et al., An experimental investigation into the tensile strength scaling of notched composites, Composites—Part A 38, 867-78 (2007).
Bažant, Z.P., Instability, Ductility and Size Effect in Strain-Softening Concrete, Journal of the Engineering Mechanics Division, ASCE, vol. 102, pp. 331-344 (1976).
ASTM International Designation 5528, Standard Test Method for Mode I Interlaminar Fracture Toughness of Unidirectional Fiber-Reinforced Polymer Matrix Composites (2007).
Bažant, Z.P. . Size effect on structural strength: a review, Archive of Applied Mechanics 69: pp. 703-725 (1999).
Bažant, Z.P. et al., Size effect on compression strength of fiber composites failing by kink band propagation, International Journal of Fracture 95: pp. 103-141 (1999).
Bažant, Z.P. et al., Size Effect on Flexural Strength of Fiber-Composite Laminates, Journal of Engineering Materials and Technology, vol. 126, pp. 29-37 (2004).
Salviato, M. et al., Experimental and numerical investigation of intra-laminar energy dissipation and size effect in two-dimensional textile composites, arXiv:1605.06174 (2016).
Salviato, M. et al., Experimental and Numerical Investigation of Intra-Laminar Energy Dissipation and Size Effect in Two-Dimensional Textile Composites, Composites Science and Technology, in press (2016).
Bažant, Z.P. et al., Direct Testing of Gradual Postpeak Softening of Notched Specimens of Fiber Composites Stablized by Enhanced Stiffness and Mass, arXiv:1607.00741 (Jul. 4, 2016).
Huges, B.P et al., The complete stress-strain curve for concrete in direct tension, RILEM Bulletin (Paris) 30, 95-97 (1966).
Evans, R.H. et al., Microcracking and Stress-Strain Curves for Concrete for Tension, Materials and Structures vol. 1, 61-64 (1968).
Heilmann, H.G. et al., Festigkeit und Verformung von Beton unter Zugspannungen, Deutscher Ausschu s für Stahlabeton, Heft 203, Berlin (1969).
Wawersik, W.R. et al., A Study of Brittle Rock Fracture in Laboratory Compression Experiments, Int. J. Rock Mech. Min. Sci. vol. 7, No. 5, 561-575 (1970).
Hudson, J.A. et al., Optimizing the Control of Rock Failure in Servo-Controlled Laboratory Tests, Rock Mech. vol. 3, pp. 217-224 (1971).
ASTMD5045 Standard Test Methods for Plane-Strain Fracture Toughness and Strain Energy Release Rate of Plastic Materials (1999).
Bažant, Z.P. et al., Bifurcation and stability of structures with interacting propagating cracks, International Journal of Fracture 53 pp. 273-289 (1992).

* cited by examiner

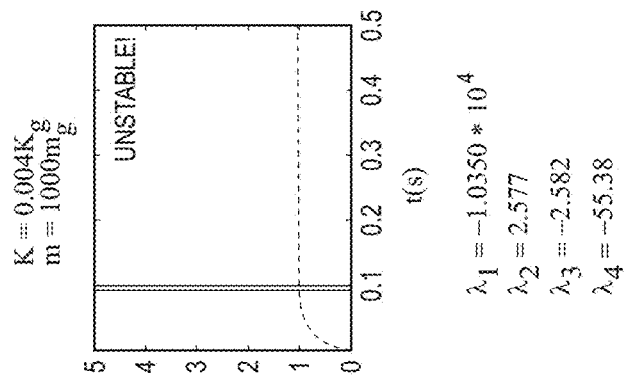
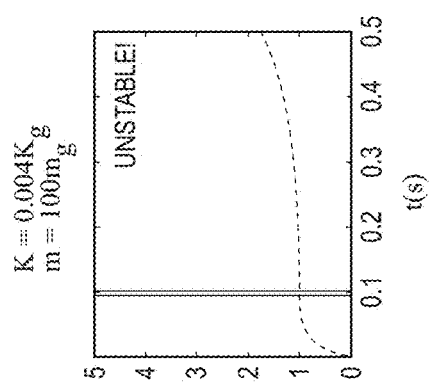
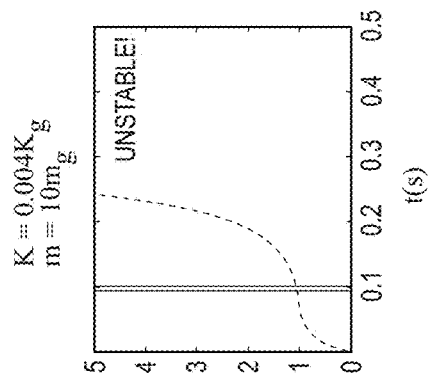
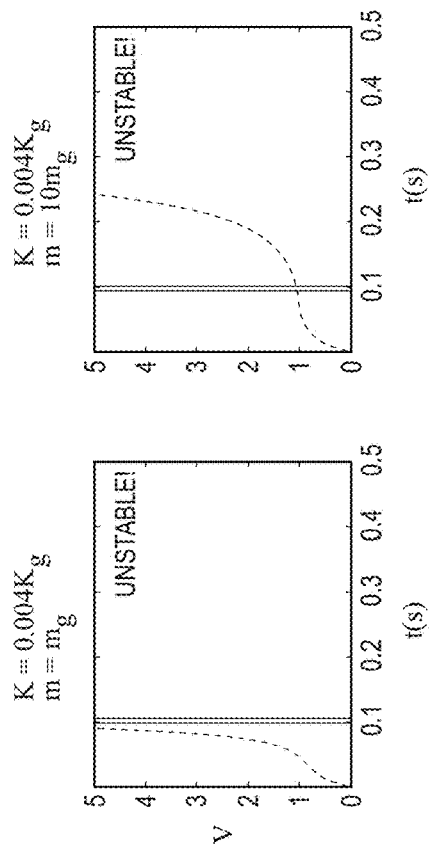

GRIPS FOR A LINEAR FRACTURE TESTING MACHINE AND METHOD OF DESIGNING SAME

CROSS-REFERENCE TO RELATED APPLICATIONS

This patent application claims the benefit of U.S. Provisional Patent Application No. 62/449,167, filed Jan. 23, 2017, the entire contents of which are incorporated by reference herein in their entirety.

CONTRACTUAL ORIGIN OF THE INVENTION

This invention was made with government support under CMMI-1439960, awarded by the National Science Foundation, and W911 NF-15-1-0240, awarded by the U.S. Army Research Office. The government has certain rights in the invention.

FIELD OF INVENTION

The present application is directed to tensile testing of materials and, more particularly, to the grips for securing a fiber composite sample to the test fixture for fracture testing, and a method for designing the grips.

BACKGROUND

The material failure criteria for fiber-polymer composites have been expressed in terms of stresses or strains. Examples are the maximum stress, maximum strain, deviatoric strain energy, and tensor polynomial criteria [1], sanctioned by a worldwide comparison exercise [2, 3, 4]. Their general applicability, however, is based on criteria applicable to plastic materials, which exhibit no strain localization instability, no spurious mesh sensitivity, no material characteristic length, and no deterministic size effect.

In reality, fiber composites are quasibrittle materials (which also include concrete—as the archetypical case, tough ceramics, rocks, sea ice, rigid foams, bone, etc.). All quasibrittle materials fail by localization of softening damage into a discrete fracture. In contrast to plasticity, they exhibit a material characteristic length. This inevitably leads to a strong energetic (or non-statistical) size effect when geometrically similar structures of different sizes are compared [5, 6, 7, 8, e.g.]. On sufficiently small scale, all brittle materials behave as quasibrittle.

Two basic types of size effects must be distinguished. Here the focus is on the "Type 2" size effect, which occurs when a large notch or stress-free crack exists at maximum load. This size effect is weak for small specimens not much larger than the periodicity of the weave or the size of the representative volume element (RVE), for which it may seem that the stress or strain failure criteria work. But with increasing structure size, there is a gradual transition to the strong size effect of fracture mechanics caused by stored energy release associated with stress redistribution during damage. It may be noted that the "Type 1" size effect occurs in structures that fail right at the initiations of a macro-crack from a damaged RVE at a smooth surface in unnotched specimens, and represents a combination of deterministic and statistical. (or Weibull) size effects (omission of the deterministic aspect led to an erroneous conclusion [e.g.][9], namely that the Weibull modulus was a geometry-dependent variable rather than a material constant).

At mesh refinement, the use of stress or strain criteria inevitably causes a loss of objectivity, spurious mesh sensitivity and convergence problems [7, 10]. For this reason, as well as fundamentally, realistic failure analysis must be based on quasibrittle fracture mechanics, which evolved since its dawn in the mid 1970s into a mature and widely accepted theory. Fracture mechanics is well accepted for delamination fracture of layered two-dimensional (unstitched) fiber-composite laminates. There is even an ASTM test to determine the corresponding fracture energy [11] (although this test has just been shown to require a correction for transitional size effect [16]).

The fact that quasibrittle fracture mechanics must apply to in-plane or flexural loading of fiber composite laminates was demonstrated by the numerous size effect tests performed, beginning in 1996 [8, 12, 13, 14, 15] on geometrically similar notched specimens. However, to many engineers and researchers the size effect tests have been unconvincing for two reasons: 1) some erroneously considered the size effect to be statistical, due to material randomness (although this is possible only for Type 1 failures); 2) others rejected the cohesive crack model because a gradual postpeak softening could never be observed in experiments. The specimens always failed explosively right after attaining the maximum load, and the load applied by the testing machine dropped suddenly to zero. The sudden drop seemed to indicate a LEFM behavior, but the LEFM clearly did not fit test data, and also suggested a snapback, but the area under the snapback curve would give a much smaller fracture energy than the LEFM testing.

A similar history occurred long ago for concrete and rock. Until the 1960s it was believed that concrete and rock explode at maximum load and the load applied by the testing machine drops suddenly to zero. Then, beginning in 1963, several researchers, including Hughes, Chapman, Hillsdorf, Rüsch, Evans and Marathe [18, 19, 20, 21] came up with the idea of using, for both tensile and compressive tests of concrete, a much stiffer loading frame and fast hydraulic servo-control. Suddenly, a gradual postpeak decline of the compressive or tensile load could be observed. Similar efforts to stabilize postpeak in compression testing of rock were made, beginning 1963, by Neville G. W. Cook and Charles Fairhurst at University of Minnesota [22, 23, 24]. The stability of postpeak was further enhanced by controlling the test electronically with a gage measuring the crackmouth opening displacement (CMOD). A servo-controlled stiff machine of MTS Corporation was built in 1967.

This discovery opened a revolution in the mechanics of concrete and rock, and was one essential factor that prompted the development of quasibrittle fracture mechanics. The stabilizing effect of machine stiffness was mathematically demonstrated by static stability analysis in [10], which led to an equation for the required machine stiffness as a function of the maximum steepness of the postpeak load-deflection curve (see also [6]).

Unfortunately, the same measures did not work for fiber composites. The same stiff frames with fast servo-control did not suffice. The CMOD control of notched compact tension specimens and of edge-notched strips was tried at Northwestern, but did not work. Neither did the control of crack tip opening displacement (CTOD).

By way of the present application (and as documented on Jul. 4, 2016, in arXiv submission [17]), it is shown that the foregoing objection is invalid, that postpeak can be measured, in a stable test, and that quasibrittle fracture mechanics with transitional size effect is perfectly applicable to fiber-polymer composites.

SUMMARY

The present disclosure has several aspects. In one aspect, grips for securing a quasi-brittle test specimen to the base and crosshead of a linear fracture testing machine are provided. The grips comprise two parallel legs extending from a base to form a generally U-shaped clevis, with the legs defining a slot for receiving the test specimen. The legs each have an aperture for receiving a pin by which the test specimen is secured to the grip. The base of the grip includes either a threaded shaft or a threaded bore for securing the grip to the testing machine.

A method for designing the grips are disclosed with respect to a static stability analysis that uses as input the softening stiffness of the sample ($K_s>0$) and the stiffness of the loading machine ($K_m>0$), by which the stiffness of the grips $K_g$ must satisfy the inequality $K_g>1/(1/K_s-1/K_m)$.

Grips designed according to the static stability analysis are configured such that if the test specimens have a tangential (incremental) stiffness $K_s<-0-$ and the linear fracture testing machine has a frame stiffness $K_m$, the grips have a stiffness $K_g$, such that the combined stiffness of the testing machine and grips $K_{mg}=1/(1/K_m+1/K_g)$, resulting in the total stiffness of the test specimen, the testing machine and the grips $K_t=1/(1/K_m+1/K_g)+K_s>-0-$, and the grips having a stiffness $K_g=1/(K_s/K_t-1/K_m+1/K_t)>-0-$. In an exemplary embodiment, $K_m=200$ MN/m, $K_s=-0.830$ MN/m, and $K_g=192.4$ MN/m, the grips having a mass of 9.419 kg.

A method for designing the grips according to a dynamic stability analysis is also disclosed that uses as input the softening stiffness of the sample ($K_s<0$), the stiffness of the loading machine frame ($K_m>0$), the mass of the sample $m_s$, the mass of the loading machine frame $m_m$, the time delay τ of the loading machine, and the PID parameters (α, β, γ) of the closed-loop control system. The stiffness and the mass of the grips must be designed such that the eigenvalues of the matrix shown in Eq. 28 below are strictly negative. In an exemplary embodiment, the grips are for testing softening CT specimens with a softening stiffness of $K_s<0.8$ MN/m, a machine frame stiffness $K_m>250$ MN/m and for a machine frame mass $m_m>500$ kg.

BRIEF DESCRIPTION OF THE DRAWINGS

FIGS. 4A, 4B, 4C and 4D are a series of four graphs of a load-point control stability analysis for various values of grip mass, $m_g$.

DETAILED DESCRIPTION

In the description that follows, a method for designing grips is disclosed based upon, first, a static stability analysis that identifies the minimum grip stiffness required for stability. Then a dynamic analysis of stability is presented to address issues related to the stabilization of postpeak softening of the test specimens Experiments performed to support the conclusions reached are described, and an example is presented of how the methods described herein can be used to design grips in accordance with the method.

Figure 1:
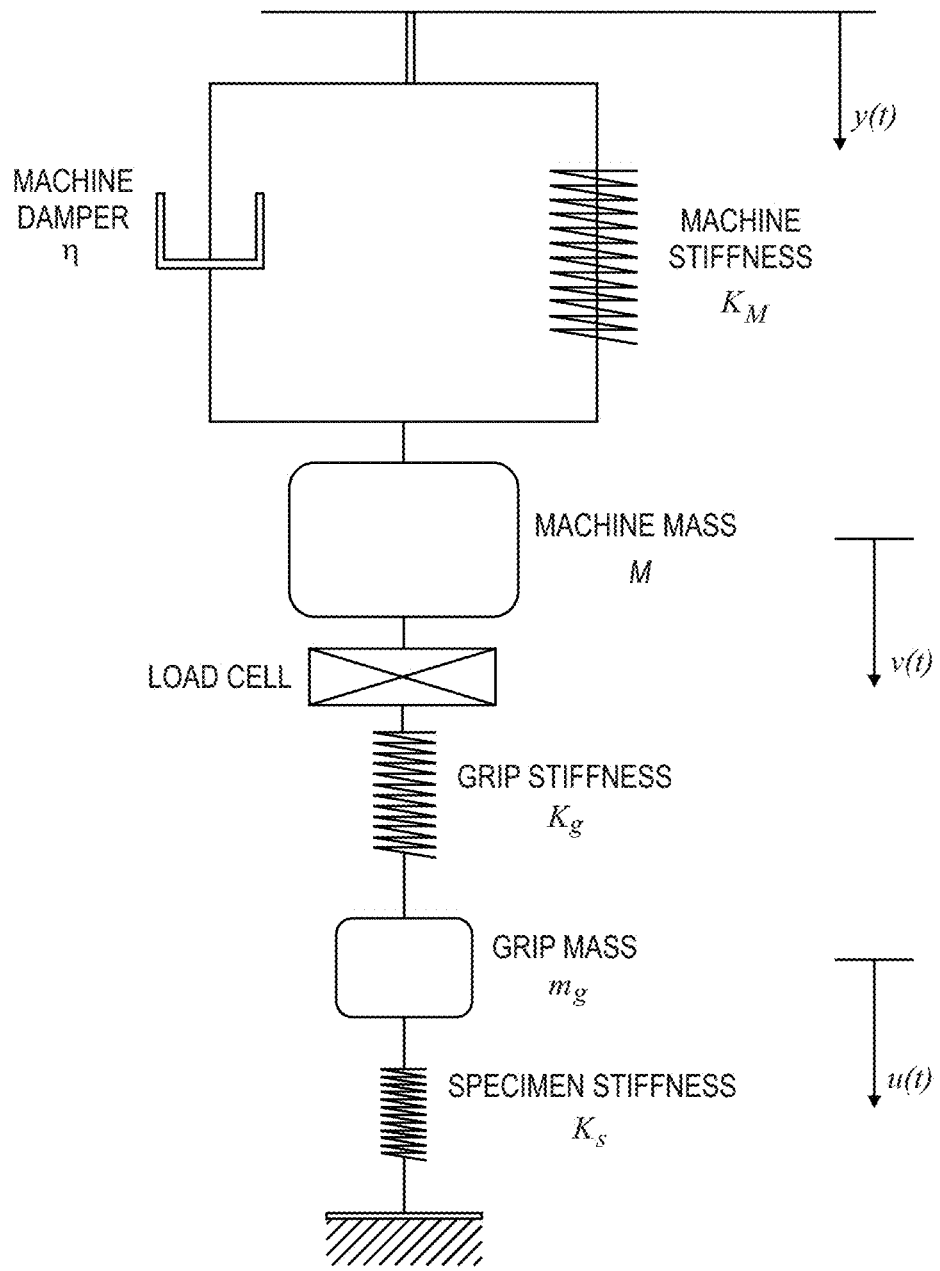
FIG. 1 is a simplified schematic of a universal servo-hydraulic testing machine.

For the purpose of static analysis, the test system can be considered as the coupling of two elements: 1) the testing machine frame of stiffness $K_m$ with the specimen grips (or fixtures) of stiffness $K_g$ forming one elastic element of stiffness $K_m$, and 2) the test specimen, of tangential (or incremental) stiffness $K_s$. FIG. 1 shows a schematic of the testing frame.

Based on the second law of thermodynamics, the test setup becomes unstable if the there exists a perturbing load that produces negative work $\Delta W$ on the test setup, thus causing an increase of entropy, $\Delta S$ (see [6, chpt. 10]). If a perturbing load $\delta P$ is applied, axially at the load-point of the test specimen while the system in equilibrium, the combined stiffness of the machine with the grips is $K_{mg}=1/(1/K_m+1/K_g)$ and the total stiffness $K_t$ resisting $\delta P$ is $K_{mg}+K_s$. The displacement under $\delta P$ in the direction of $\delta P$ is $\delta v=\delta P/K_t$, and $$\Delta W = -T\Delta S = \frac{1}{2}\delta P \delta v = \frac{1}{2}K_t(\delta v)^2 \qquad (1)$$

where T=absolute temperature. The equilibrium of the system is stable if and only if $\Delta W>0$, which requires that $K_t>0$ or $$K_t = \frac{1}{1/K_m+1/K_g} + K_s > 0 \qquad (2)$$

Figure 2:
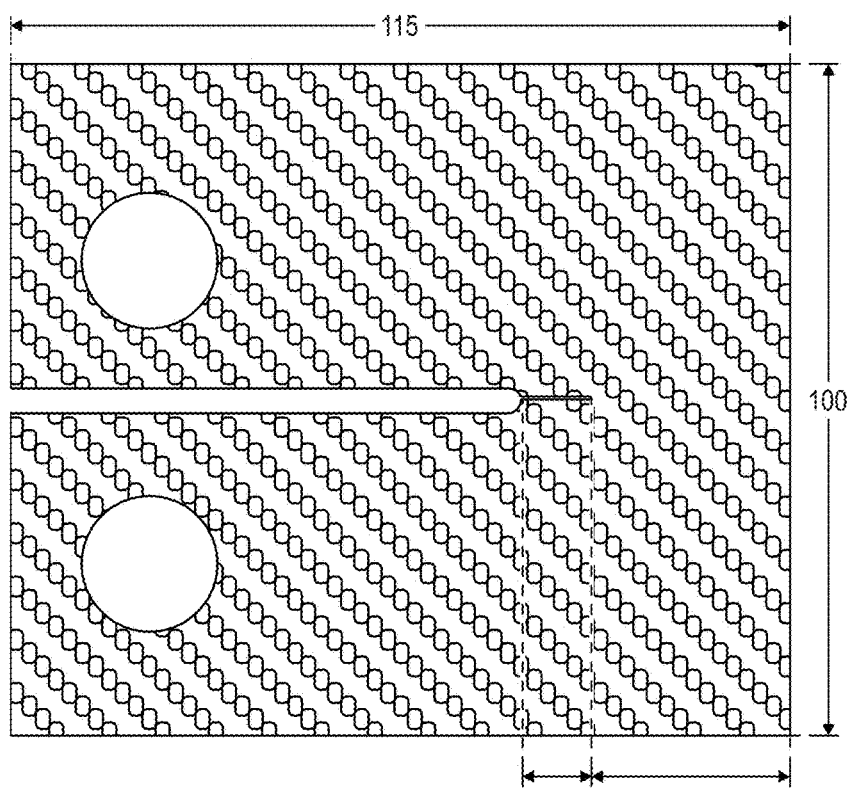
FIG. 2 shows the dimensions of a 2D woven composite specimen.

Considering a typical 20 ton testing machine (e.g., MTS) used in the testing of composites and a typical compact tension specimen consisting of 24 layers of woven carbon fiber epoxy composites for a total thickness of 5.4 mm (see FIG. 2), the typical characteristics are:
Machine frame stiffness: $K_m$=260 MN/m;
Stiffness of standard specimen grips: $K_g$=0.768 MN/nm;
The steepest slope of the measured postpeak load-deflection curve of the test specimen: $K_s$=−0.830 MN/m;
Mass of machine frame: $m_m$=500 kg;
Mass of grips (or fixtire $m_g$=0.919 kg;
Characteristic halftime of machine hydraulics delay: τ=0.02 s (de-fined as the time to approach halfway to a suddenly changed setting of electronic control).
Using these value, from Eq. (2), it is determined that $$K_t = -0.06426 \text{ MN/m} < 0 \tag{3}$$

i.e., the tested specimen is unstable. This would suggest that it is impossible to observe gradual postpeak softening in tensile tests of fiber composites.

However, this does not take into account the effect of grip stiffness. It has generally been assumed that the standard grips provided by the manufacturers are stiff enough. But comparison of $K_g$ with $K_m$ suggests otherwise. It was, therefore, decided to produce grips (FIG. 3), with the following stiffness and mass;
$\tilde{K}_g$=192.4 MN/m(=74% $K_m$)
$\tilde{m}_g$=9.419 kg (=10 $m_g$)
Compared to the current standard grips, they are about 10-times heavier and 250-times stiffer. Eq. (2) gives:

$$K_t = 109.6 \text{ MN/m} > 0 \tag{4}$$

By which stability is achieved.

Using these grips, the composite compact tension specimens (FIG. 3) exhibited stable progressive softening, and not only under CMOD control but also under load-point control. The grips overcame the feature that the fracture energy $G_f$ deduced from the size effect tests was much larger than the maximum possible area under a snapback curve. In fact, the area indicated by $G_f$ required a rather gradual progressive softening, and this is what is now observed with the new grips.

From Eq. (2), one can obtain the minimum grip stiffness, necessary for stability, based on the estimated steepest postpeak slope $K_s$:

$$[K_g]_{min} = \frac{1}{1/|K_s|_{max} - 1/K_m} \quad (K_s < 0) \tag{5}$$

Thus, using the static analysis above, and by manipulation of Equation (5), grips according to the present disclosure have a tangential (incremental) stiffness $K_s$<−0− to the base and crosshead of a linear fracture testing machine having a frame stiffness $K_m$, the grips having a stiffness $K_g$, such that the combined stiffness of the testing machine and grips $K_{mg}$=1/(1/$K_m$+1/$K_g$), and the total stiffness of the test specimen, the testing machine and the grips $K_t$=1/(1/$K_m$+1/$K_g$)+$K_s$>−0−, and the grips have a stiffness $K_g$=1/($K_s$/$K_t$−1/$K_m$+1/$K_t$)>−0−.

Postpeak softening has typically been stabilized by controlling the Crack Mouth (or Crack Tip) Opening Displacement (CMOD or CTOD). If w is the relative displacement across the crack mouth or across the crack-tip region, and F denotes a fictitious force working on w (although in reality F=0), the incremental (or tangential) cross compliance $C_{sc}$ between the load, P, and displacement w is derived by considering the relations:

$$du = C_s dP + C_{sc} dF \tag{6}$$

$$dw = C_{sc} dP + C_{cc} dF \tag{7}$$

where P=applied force; $C_s$=1/$K_s$=direct (load-point) incremental (or tangential) compliance of the specimen. According to the LEFM [7, e.g.], $$C_{sc} = \frac{2}{bDE'} \int_0^\alpha k(\alpha') k_c(\alpha') d\alpha' \tag{8}$$

where $\bar{\alpha}$=α/D, α=crack length, D), b=specimen dimension (or size) and width; k(α),$k_c$(α)=dimensionless stress intensity factors due to applied load P and to fictitious load F; k=$K_I b \sqrt{D}$/P where $K_I$=actual stress intensity factor; for plane stress E'=E=Young's modulus, and for plane strain E'=E/(1−$v^2$) where v =Poisson ratio. Because F=0, Eqs. (6)-(7) reduce to du=$C_s$dP and dw=$C_{sc}$dP or $$du = r_{sc} dw, \; r_{sc} = \frac{C_s}{C_{sc}} \tag{9}$$

The same equations apply to CTOD control, if w is redefined as the crack tip opening displacement.

The advantage of using CMOD or CTOD control is that, during the fracture test, w always increases. So, by controlling w, the postpeak softening can be measured even if the specimen is unstable under load-point control. But there is a caveat—the response of testing machine with its hydraulics must be fast enough. For notched concrete and rock specimens tested in the servo-controlled stiff machines introduced since 1963 it has been fast enough. But for strong and very light specimens, such as those of woven laminates, it has not been fast enough, since all the attempts to measure the postpeak by means of CMOD of CTOD control have failed. A dynamic analysis of stability (as thermodynamics applies to equilibrium states only) explains why.

The inability to obtain a stable postpeak softening under CMOD or CTOD control has been attributed to an unspecified peculiar property of composites. However, the obtaining of a stable postpeak with the grips obtained by the static analysis described above shows that there is nothing peculiar in the material behavior of composites. The most likely explanation of why CMOD alone cannot control the postpeak test is that the response of hydraulics is not fast enough (even with the optimal PID setting). A dynamic analysis of the test setup, first as an open system, confirms this.

The test setup may be idealized as shown in FIG. 1, where u(t) is the load-point displacement of the test specimen; v(t) is the displacement at the attachment of the grips (or fixture) to the loading frame, and y(t) is the input from the electronic control, representing the prescribed load-displacement history (t=time). The effective mass of the machine frame is denoted as M, and the mass of the grips as $m_g$, including the mass of the specimen (which is, however, negligible in the case of composites). The mass and stiffness of the load cell are considered to be included in M and $K_M$.

To control the test, the controller of the machine sends a signal to the servo-valve. The hydraulic pressure on the piston increases and the piston moves, but not immediately.

The halftime, $\tau$, of the hydraulics response delay, $\tau$, which is of the order of 0.02 s (and is assumed to correspond to the optimized PID setting), may be modeled by a damper of viscosity constant $$\eta = K_m \tau \qquad (10)$$

Because the system can be considered incrementally linear, it will suffice to analyze the response to a sudden unit change of y, i.e., y=H(t) where H denotes the Heaviside step function. Because only infinitely small increments are considered, the response may be considered to be linear and $K_s$ to be constant, characterizing the steepest postpeak slope of the postpeak load displacement curve ($K_s$<0). We also assume that no unloading would occur (because, for unloading, $K_s$ would switch to a positive value).

The equations of motion can be derived from the Lagrange equations:

$$\frac{\partial}{\partial t}\left(\frac{\partial L}{\partial \dot{v}}\right) - \frac{\partial L}{\partial v} + \frac{\partial \mathcal{D}}{\partial \dot{v}} = 0 \qquad (11)$$

$$\frac{\partial}{\partial t}\left(\frac{\partial L}{\partial \dot{u}}\right) - \frac{\partial L}{\partial u} + \frac{\partial \mathcal{D}}{\partial \dot{u}} = 0 \qquad (12)$$

where $L = T - V$ (13)

$$T = \frac{1}{2} M \dot{v}^2 + \frac{1}{2} m_g \dot{u}^2 \qquad (14)$$

$$V = \frac{1}{2} K_M (v - y)^2 + \frac{1}{2} K_g (v - u)^2 + \frac{1}{2} K_s u^2 \qquad (15)$$

$$\mathcal{D} = \frac{1}{2} K_M \tau (\dot{v} - \dot{y})^2 \qquad (16)$$

where the superior dots denote derivatives with respect to time t. Eqs. (11) and (12) yield the following equations of motion:

$$M\ddot{v} + K_M(v-y) + K_M\tau(\dot{v}-\dot{y}) + K_g(v-u) = 0 \qquad (17)$$

$$m_g \ddot{u} + K_g(u-v) + K_s u = 0 \qquad (18)$$

where $K_M \tau$ was substituted. It is convenient to rewrite the equations of motion in the phase space by introducing new variables:

$$x_1 = u, \; x_2 = \dot{u}, \; x_3 = v, \; x_4 = \dot{v} \qquad (19)$$

Substitution into the equations of motion gives a system of first-order ordinary linear differential equations in matrix form:

$$\begin{Bmatrix} \dot{x}_1 \\ \dot{x}_2 \\ \dot{x}_3 \\ \dot{x}_4 \end{Bmatrix} = \begin{bmatrix} 0 & 1 & 0 & 0 \\ -\frac{K_g + K_s}{m_g} & 0 & -\frac{K_g}{m_g} & 0 \\ 0 & 0 & 0 & 1 \\ \frac{K_g}{M} & 0 & -\frac{K_M + K_g}{M} & -\frac{K_M \tau}{M} \end{bmatrix} \begin{Bmatrix} x_1 \\ x_2 \\ x_3 \\ x_4 \end{Bmatrix} + \begin{Bmatrix} 0 \\ 0 \\ 0 \\ \frac{K_M}{M} y + \frac{K_M \tau}{M} \dot{y} \end{Bmatrix} \qquad (20)$$

The homogeneous part of this first-order matrix differential equation is satisfied by functions of the form $x_n = a_n e^{\lambda t}$ (n=1, 2, 3, 4). Substitution into the homogeneous part of the foregoing matrix differential equation yields a homogeneous matrix algebraic equation for the column matrix of $a_n$. It has a nonzero solution if and only if $\lambda$ is equal to the eigenvalues of the square matrix in Eq. (20). The solution is stable if and only if, for all the eigenvalues, $$Re(\lambda) < 0 \qquad (21)$$

For calculations, the aforementioned machine and test properties with the standard grips is considered. Then the following column matrix of eigenvalues is calculated:

$$\{\lambda\} = \begin{Bmatrix} 80.65 \\ -1.035 \cdot 10^4 \\ -77.17 \\ -53.87 \end{Bmatrix} \qquad (22)$$

The presence of a positive eigenvalue, $\lambda_1$, indicates that, with the standard grips, the test of postpeak is unstable, which means that postpeak softening cannot be observed, as is known from experience. Also note that the eigenvalues are real, which means that the stability loss is a divergence rather than flutter (oscillatory instability). Thus the static stability check in Eq. (3) is sufficient.

Now, considering the new grips of mass $m_g = 10 m_{g0} = 9.419$ kg and stiffness $K_g = 10 K_{g0} = 2.6 \cdot 10^9$ N/m (FIG. 3), with all the other parameters remain the same, the calculations yield the eigenvalue matrix (with $i^2 = -1$):

$$\{\lambda\} = \begin{Bmatrix} -15.78 + 4.52i \cdot 10^3 \\ -15.78 - 4.52i \cdot 10^3 \\ -1.032 \cdot 10^4 \\ -50.129 \end{Bmatrix} \qquad (23)$$

All Re($\lambda$)-values are negative. So the specimen is stable, even under load-point control. This confirms the previous finding by static stability analysis, Eq. (4).

CMOD or CTOD control would work with the standard grips if the response of the controls were infinitely fast. However, with a hydraulic system this is impossible. The specimen accelerates fast in dynamic motion before the hydraulics can adjust the displacement.

The way to slow down the acceleration is to increase the mass to the grips. If the grip mass $m_g$ is increased to $\overline{m}_g = 10 m_g$, $100 m_g$ and $1000 m_g$, without increasing the grip stiffness, the sets of eigenvalues achieved are listed under the diagrams of FIG. 4. All of these sets include an eigenvalue with Re($\lambda$)>0, which means the specimens are unstable—but unstable under controlled load-point displacement.

With a view of CMOD control, the response of the system for input y(t) =H(t) (Heaviside step function) is calculated under four initial conditions $u = \dot{u} = v = \dot{v} = 0$. The solution is obtained as a sum of the particular solution and a linear combination of four eigenvectors. The response curves of u(t) are plotted in the four diagrams of FIG. 4. Note that, with increasing grip mass, the time at the onset of sharp exponential acceleration of displacement u(t) (briefly 'onset time') greatly increases.

To compare the onset time with the performance of the hydraulics, vertical lines are plotted in FIG. 4 at time of 0.1 s, which is 5-times longer than the halftime of the hydraulics delay, by which time the CMOD control should be able to enforce the specified load-point displacement u with sufficient accuracy.

In the first diagram of FIG. 4, which corresponds to the standard (light) grips, the rise of exponential acceleration of u(t) begins much before the critical time of 0.01 s. Obviously, the controls are too slow to prevent this acceleration, which inevitably leads to sudden failure. However, as seen in the third diagram, the grip mass of 100 $m_g$ postpones the acceleration well beyond 0.1 s, and here the hydraulics controlled by the CMOD should evidently be able to impose the required load-point displacement.

According to the second diagram for 10 $m_g$, it seems the exponential acceleration could also be prevented, but better informed analysis of the hydraulic system and trial testing may be needed. The fourth diagram, for 1000 $m_g$, is obviously overkill.

Figure 5:
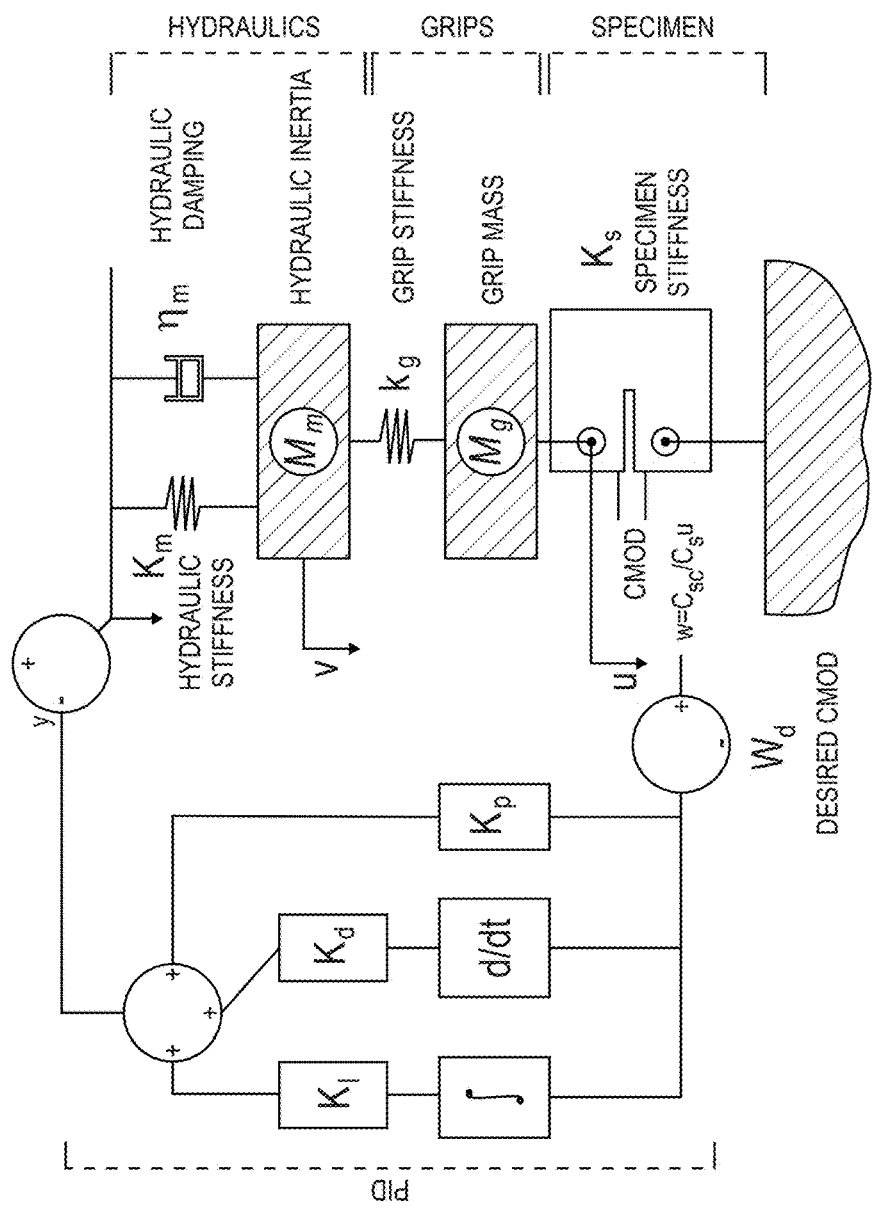
FIG. 5 is a schematic of the machine and testing setup including the PID control.
Figure 6A:
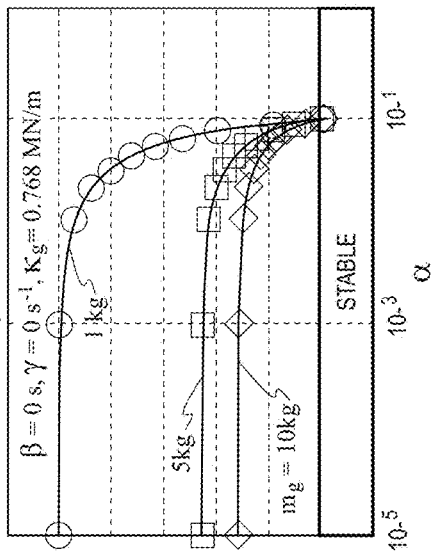
FIGS. 6A, 6B, 6C and 6D are a series of graphs showing the effect of grip mass on a) an open system, b) proportional control, c) differential control, and d) integrative control, respectively.
Figure 6B:
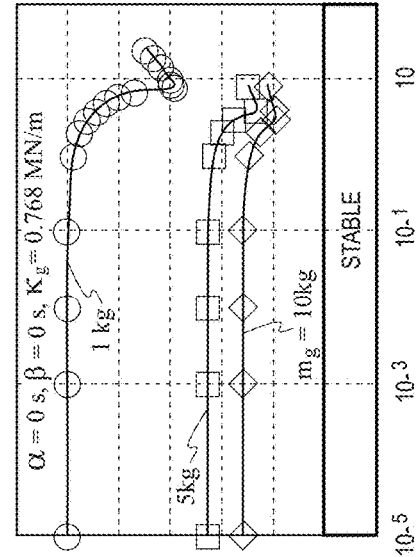
Figure 6C:
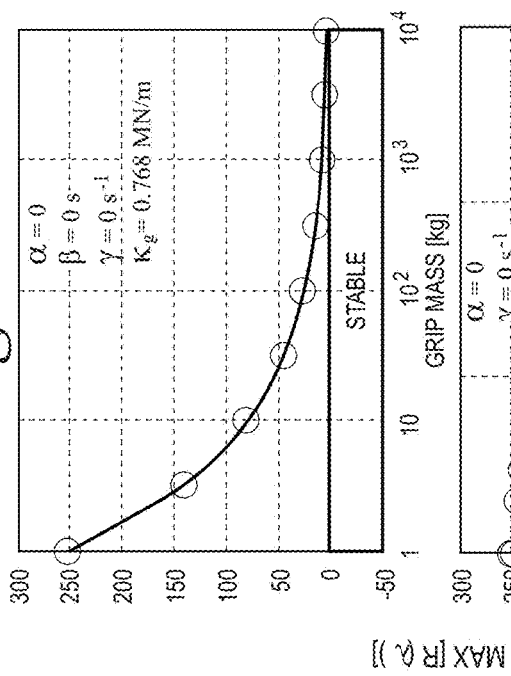
Figure 6D:
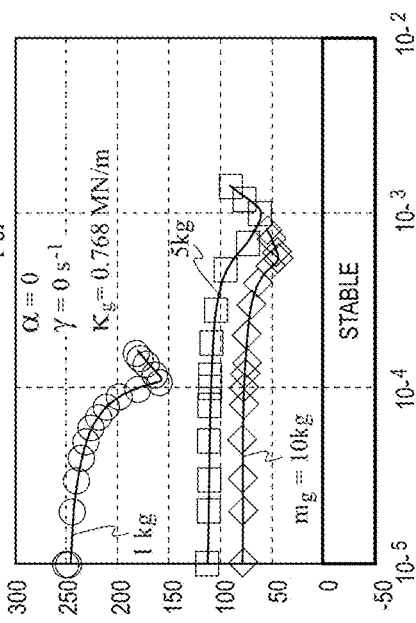
Figure 7A:
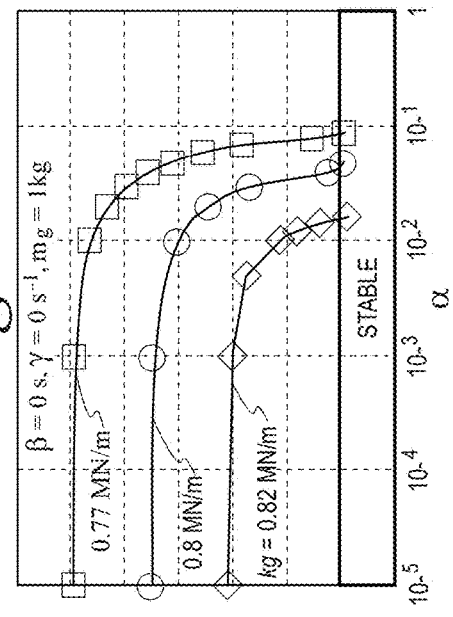
FIGS. 7A, 7B, 7C and 7D are a series of graphs showing the effect of grip stiffness on a) an open system, b) proportional control, c) differential control, and d) integrative control, respectively.
Figure 7B:
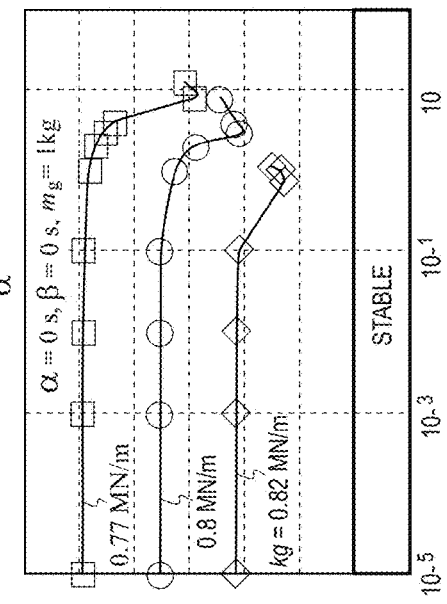
Figure 7C:
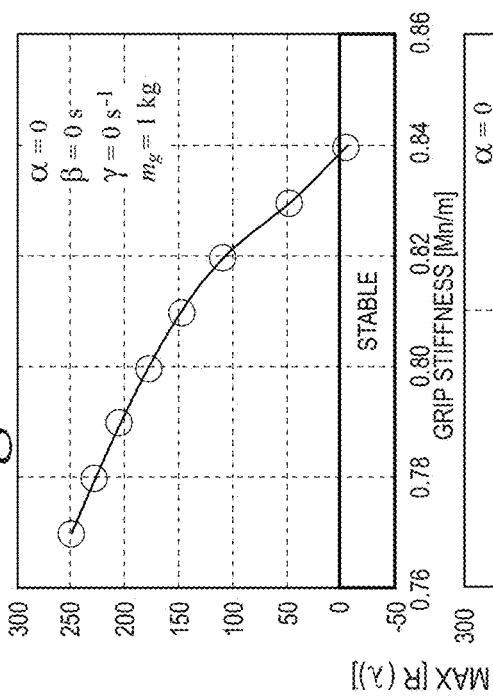
Figure 7D:
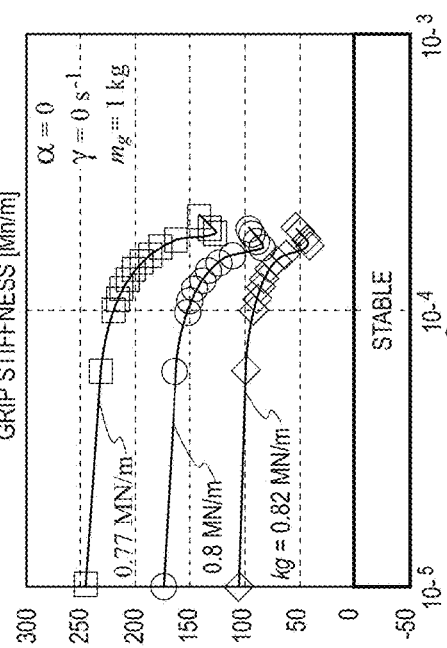

The closed-loop control of the modern testing machines is based on a Proportional-Integrative-Differential (PID) signal of the error $w_D - w$ where $w_D$=desired Crack Mouth Opening Displacement (CMOD) and w=CMOD measured by the extensometer; see the schematic of the control loop in FIG. 5.

Combining Eqs. (6) and (7) and integrating over a small time interval with constant tangential stiffnesses, one gets $w = C_{sc}/C_s u$ where $u(0) = w(0) = 0$ may be assumed. Accordingly, the equations of motion of the system may be written as:

$$\begin{cases} m\ddot{u} + K_g(u - v) + K_s(u) = 0 \\ M\ddot{v} + K_M[\zeta(v, u, y) + \tau\dot{\zeta}(v, u, y)] + K_g(v - u) = 0 \\ \zeta(v, u, y) = v - y + \left(\frac{C_{sc}}{C_s}u - w_D\right)K_P + \left(\frac{C_{sc}}{C_s}\dot{u} - \dot{w}_D\right)K_D + \\ \qquad K_I \int_0^t \left(\frac{C_{sc}}{C_s}u - w_D\right)dt' \end{cases} \quad (24)$$

where $K_p$ is the proportional gain of the PID control, and $K_g$ is the stiffness of the grips. Introducing the transformation:

$$x_1 = u, \ x_2 = \dot{u}, \ x_3 = v, \ x_4 = \dot{v}, \ x_5 = \int x_1 dt \quad (25)$$

the system of equations becomes:

$$\begin{cases} \dot{x}_1 = x_2 \\ \dot{x}_2 = -\frac{1}{m}[K_g(x_1 - x_3) + K_s(x_1)] \\ \dot{x}_3 = x_4 \\ \dot{x}_4 = -\frac{1}{M}\{K_M[x_3 + \alpha x_1 + \beta x_2 + \gamma x_5] + \\ \quad K_M \tau\left[x_4 + \alpha x_2 - \frac{\beta}{m}K_g(x_1 - x_3) - \frac{K_g}{m}\beta x_1 + \gamma x_1\right] + \\ \quad K_g(x_3 - x_1)\} - K_M \chi(y, w_D) \\ \dot{x}_5 = x_1 \end{cases} \quad (26)$$

where $$\alpha = \frac{C_{sc}}{C_s}K_p, \ \beta = \frac{C_{sc}}{C_s}K_d, \ \gamma = \frac{C_{sc}}{C_s}K_i \text{ and}$$

$$\chi = \left[y - \alpha w_D - \beta \dot{w}_D - \gamma \int w_D dt' + \tau(\dot{y} - \alpha \dot{w}_D - \beta \ddot{w}_D - \gamma w_D)\right] \quad (27)$$

The foregoing system is stable if the linearized system is stable [6, chpt. 3]. Stability requires that all the eigenvalues $\lambda$ of the matrix of equations (26), given below, be negative:

$$\begin{bmatrix} -\lambda & 1 & 0 & 0 & 0 \\ -\frac{1}{m}\left(K_g + \frac{\partial K_s}{\partial x_1}\right) & -\lambda & \frac{K_g}{m} & 0 & 0 \\ 0 & 0 & -\lambda & 1 & 0 \\ R_1 & -\frac{\beta K_M}{M} & R_2 & -\frac{K_M \tau}{M} & -\frac{K_M \gamma}{M} - \lambda \\ 1 & 0 & 0 & 0 & -\lambda \end{bmatrix} \quad (28)$$

where $$R_1 = \frac{K_g - \alpha K_M}{M} + \frac{K_M \tau}{M}\left[\gamma + \beta \frac{\partial K_s/\partial x_1 + K_g}{m}\right] \quad (29)$$

$$R_2 = -\frac{K_M + K_g}{M} + \frac{\beta \tau K_g K_M}{mM} \quad (30)$$

The calculation results shown in FIGS. 6 and 7 show the effects of the mass and thickness of the grips, respectively. The stiffness has a big effect on stability but, at first surprisingly, the mass has none. That calls for discussion from a different viewpoint—controllability.

According to Liapunov's definition of stability [6, Sec. 3.5], the response $x_i(t)$ of a dynamic system with initial state $x_i^0$ is stable if, for an arbitrarily small positive number $\epsilon$, there exists a positive number $\delta$ such that the response to any change of the initial state $x_i^0$ smaller than $\delta$ will never deviate from $x_i(t)$ by more than $\epsilon$. But, in an open system with active input y(t), what matters is the controllability.

A state $x'_i$ is controllable at time t' if there exists an input y(t) that transfers the state $x_i(t)$ from $x'_i$ to the specified state $x'_i$ within some finite time interval $\Delta t$. If this is true for all t', the system is controllable. Generally, a stable system is controllable, but a system can be controllable even if it is unstable (note that modern aircraft fly with wings that are unstable but controllable), while, as we showed, the mass has no effect on stability, it has a big effect on controllability, as is obvious from FIG. 4. The following five observations can be made:

1. Although increasing the mass of the grips decreases the most critical eigenvalue (a tenfold increase of $m_g$ reduces the most critical eigenvalue by 70%), stability can be reached only with infinite mass.
2. The proportional gain of the PID control, $K_p$, is the one having the greatest effect on stability. Increasing the mass of the grips does not increase the range of values of $K_p$ leading to stability.
3. The derivative and integrative gains play a secondary role in stability compared to the proportional gain. Increasing $m_g$ does not have a very significant effect on these parameters.
4. A huge effect of grip stiffness stability (exemplified here by stability attainment, even without CMOD control, with a mere 9% stiffness increase) is not the only effect of grip stiffness, $K_g$. A further effect is a significant contribution to the proportional gain. Increasing the stiffness by 2% reduces the minimum value of $K_p$ leading to stability by 80%, thus making the test control much easier.
5. On the other hand, the grip stiffness does not have a strong effect on the integrative and derivative gains.

Figure 3B:
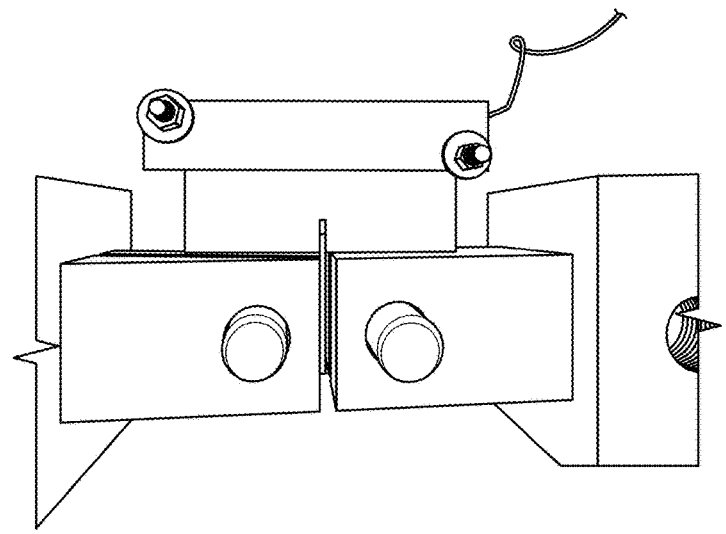
FIG. 3B depicts the grips designed to achieve stable post peak.
Figure 3A:
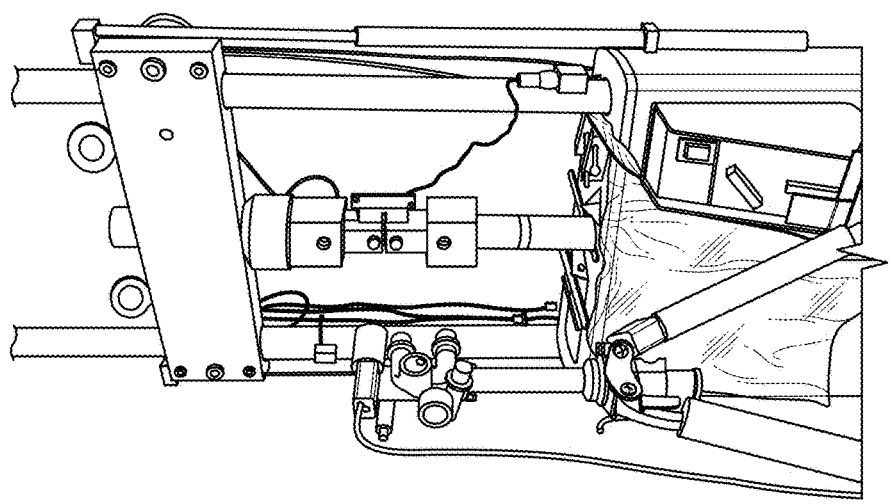
FIG. 3A depicts the experimental setup considered in the analysis.

Experimental Verification of Stable Postpeak Softening of Compact Tension Specimens FIG. 3 shows the compact-tension fracture specimen of woven carbon-epoxy specimens used to study the postpeak behavior and determine the fracture energy $G_f$ of the material and the general view of the test setup in a MTS testing machine.

Figure 8B:
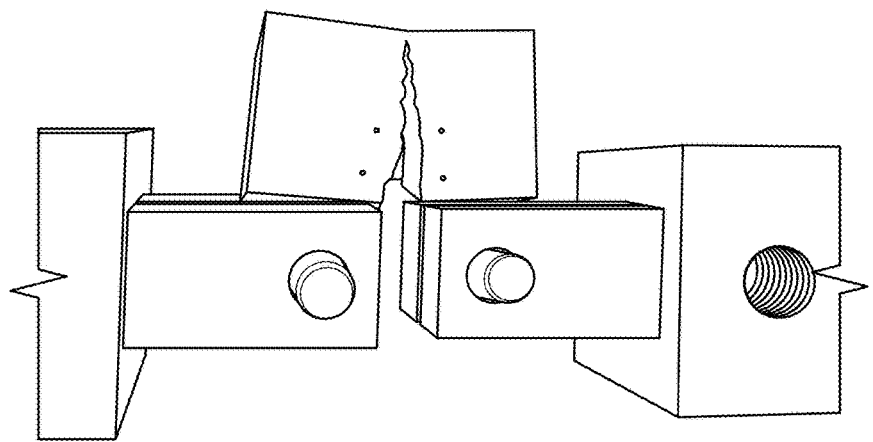
FIG. 8B depicts grips designed according to the present application and having increased stiffness and mass.
Figure 8A:
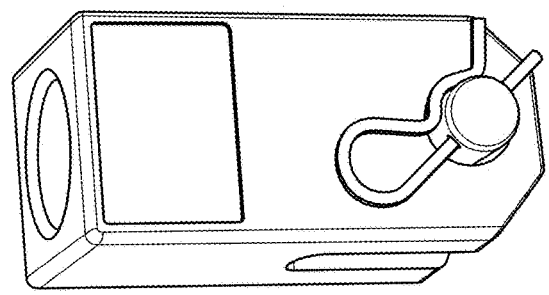
FIG. 8A depicts a MTS® standard fracture mechanics clevis grip.

FIG. 8 shows the photos of the current standard grips (on the left) and of the proposed massive grips (on the right) that successfully stabilized the postpeak.

FIG. 9 demonstrates several stable postpeak load-delection diagrams measured with the proposed stiff grips on the compact-tension specimens.

Agreement of $G_f$ from Size Effect Tests with $G_f$ from the Area Under Complete Load-Displacement Curve The area A under the complete stable load-displacement curve of the fracture specimen allows determining the fracture energy, $G_f$, of the material; $G_f=A/Lb$ where l=length of the broken ligament and b=specimen thickness (provided that energy dissipation outside the fracture is negligible).

Figure 10:
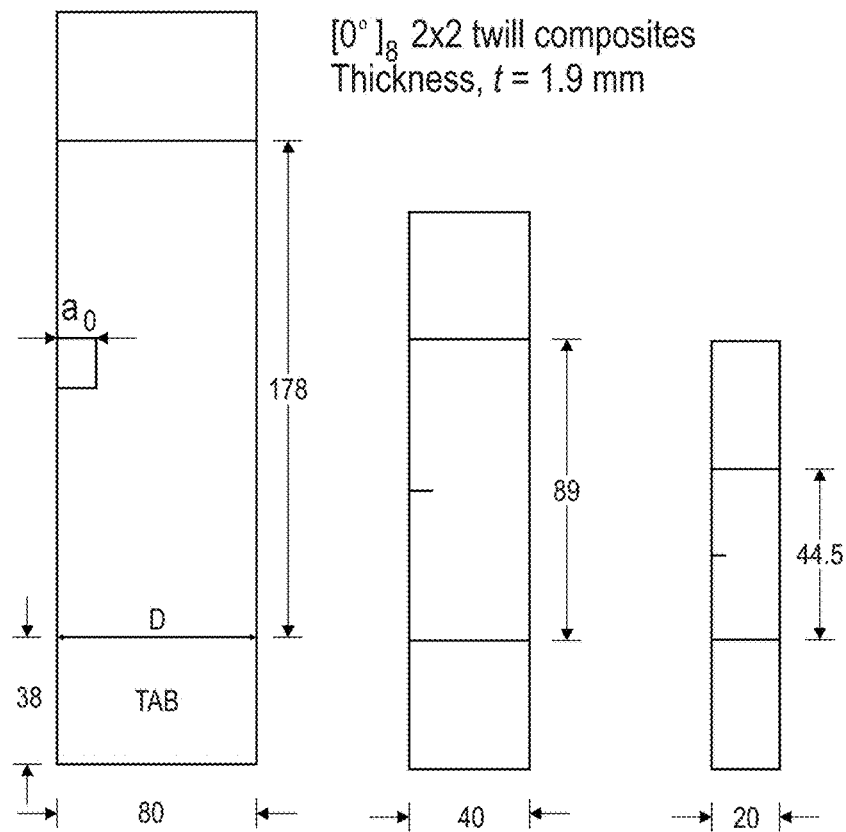
FIG. 10 depicts the geometry of three sizes of Single Edge Notched Tension (SENT) specimens used in the testing (units: mm).

Another, easier, way to determine the fracture energy is the size effect method [7]. For this purpose it was more convenient to use tensile tests of geometrically similar edge-notched strip specimens of three different sizes, as shown in FIG. 10. Because this method uses only the maximum loads and the postpeak softening is not needed, it suffices to conduct the tests with the standard grips, even though they failed right after the peak load. The fracture energies obtained from the size effect and from the postpeak were respectively: from size effect: $G_f$=73.7 N/m and from postpeak:

$$G_f=78 \text{ N/m} \tag{31}$$

It is notable that the difference between these two values is only 5.8%.

Nonexistence of Snapback and of Conflict with Size Effect

Because it was impossible to observe postpeak softening it has been believed for decades that the fracture specimens of composites exhibit a severe snap-back. Based on the stiffening the grips as set forth above, it can now be seen that this view was incorrect. The misconception of snapback further shed false doubts on the applicability of fracture mechanics to fiber composites. The area under the supposed snapback curve, which must in any case be smaller than the area under a load-deflection curve with sudden vertical load drop from the peak-load point, gave a fracture energy much smaller than that deduced from the size effect, or from the measured drop of complementary energy of test specimen.

For some investigators, this severe mismatch was another reason to consider quasibrittle cohesive fracture mechanics as inapplicable to fiber composites. Now we see that this interpretation was mistaken.

The present analytical and experimental results, and especially Eq. (31), prove that fracture mechanics is equally applicable to fiber composites.

Determining why the Postpeak in Delamination Fracture Tests has been Stable

To determine the delamination fracture energy of the same carbon composite, the ASTM standard test specimen [11] was used. In these tests, the gradual postpeak softening was stable, even with the standard grips. The explanation is that the delamination specimens are much softer than the compact tension specimens. If $|K_s|$ is small enough, $K_t$ ceases to be negative since the first term in Eq. (2) is always positive. We see that the required stiffness of the grips increases with the stiffness of the fracture specimen.

CONCLUSION

1. The specimen grips (or fixtures) of the contemporary hydraulic servo-controlled testing machines do not have sufficient stiffness and mass to enable stable measurement of postpeak softening of fracture specimens of very strong and very light materials such as fiber composites.

2. By stability analysis based on the second law of thermodynamics, it is shown that the cause of pervasive failure to observe postpeak softening during the past half century decades of composites testing has been the instability due to insufficient stiffness and mass of the specimen grips.

3. Based on static stability analysis of the test setup, it is proposed to use grips that are stiff by about two orders of magnitude. Calculations show that, in this way, stability is achieved.

4. Experiments on compact-tension fracture specimens of woven fiber-polymer composites confirm the observability of stable postpeak, not only for the CMOD control but even for the load-point displacement control.

5. The grip stiffness required for stability increases with the stiffness of the fracture specimen.

6. Calculations of the eigenvalues of the equations of motion of the test setup confirm that the grip stiffness has a huge effect on static as well as dynamic stability, makes the PID control much easier.

7. Calculations also indicate a large effect of the increase of mass of the grips on controllability of the postpeak response under PID control, although the effect on stability is nil.

8. Calculations further they indicate that, if a sufficient mass is rigidly attached to the existing soft grips, the postpeak response under PID control of the CMOD should become controllable.

9. The present stability analysis also explains why the switch in the 1960s to far stiffer testing frames sufficed to stabilize the postpeak softening in concrete and rocks, but not in composites. The specimens of concrete and rock are generally far more massive and their attachments (consisting of flat contacts, glued in the case of tension) have naturally been far stiffer than those used for fiber composites.

10. The previous view that the impossibility of measuring postpeak softening necessarily implied a severe snapback is not correct. In the usual compact-tension specimens there is no snapback.

11. The previous inference that the smallness of the area under the supposed snapback curve conflicted with $G_f$ measured from the size effect or from the energy release was thought to invalidate fracture mechanics. This inference was false.

12. The present results prove that quasibrittle fracture mechanics, with finite fracture process zone and a transitional size effect, is perfectly applicable to fiber composites.

13. The present results also prove that the previously widespread use of plasticity-based failure envelopes in terms of stress or strain has not been correct.

EXPERIMENTS

Materials

Experiments were conducted on woven composite specimens manufactured by compression molding. A DGEBA-based epoxy resin was chosen as polymer matrix whereas the reinforcement was provided by a twill 2×2 fabric made of carbon fibers. The material was characterized following the ASTM standard procedures [25] for testing under compact tension. The material was a [0°]8 lay-up with a constant thickness of approximately 1.8 mm.

Further experiments were conducted on fiberglass reinforced polyester (FRP) composite, with the thickness of about 10 mm.

Specimen Characteristics

The modified Compact Tension (CT) specimen geometry was developed to produce stable crack growth so that the composite damage zone could be investigated. Initially, a 2 mm width notch was created by using diamond band saw. Then, the notch was extended by using artistic wire saw in order to create a shape notch tip of 0.2 mm in radius. The CT specimen with a sharp notch tip is stable under displacement control and is large enough so that the boundaries do not greatly affect the damage zone size or shape.

The specimen was loaded in tension through pins located above and below the notch. It was found that the pin holes cannot be made using steel drill bits because the carbon fiber is harder than the steel from which the drill is made. To avoid damage due to fiber tear-out and delamination around the holes caused by steel drill bits, abrasive cutting with tungsten grinding bits for nonmetals was used to create these holes. The specimen thickness of 5.4 mm sufficed to prevent of the woven composite material.

Furthermore, intra-laminar size effect tests were conducted on single-edge-notched tension (SENT) specimens (see FIG. 10), using a [0°]8 lay-up with a constant thickness of approximately 1.9 mm. The SENT specimens were preferred to double-edge notched tension (DENT) specimens because in these specimens the response path bifurcates such that only one of the two cracks can propagate, causing asymmetric response [26].

SENT specimens of three sizes (three for each size), geometrically scaled in two-dimensions in the ratio 1:2:4, were tested. The specimen lengths, L+2L$_t$ were, respectively, 120.5, 165.0, 254.0 ram, the gauge lengths 44.5, 89.0, 178.0 mm, the widths 20, 40, 80 mm, and the notch lengths 4, 8, 16 mm. The thickness was 1.9 mm, and the tab length L$_t$=38 mm, the same for all the sizes. The glass-epoxy tabs, for gripping purposes, were not scaled because they have no appreciable effect on the store energy release and because fracture always occurs away from the grips.

The first half of the notch of SENT specimens was cut by means of a diamond-coated bend saw which provided a width of roughly 1 mm. The second half of the notch was cut by a diamond-coated miniature blade, thanks to which a notch width of only 0.2 mm was achieved in all cases. Accordingly, the resulting crack tip radius was 0.1 mm, about 70 times smaller than the size of a Representative Unit Cell (RUC) of the material.

Figure 11A:
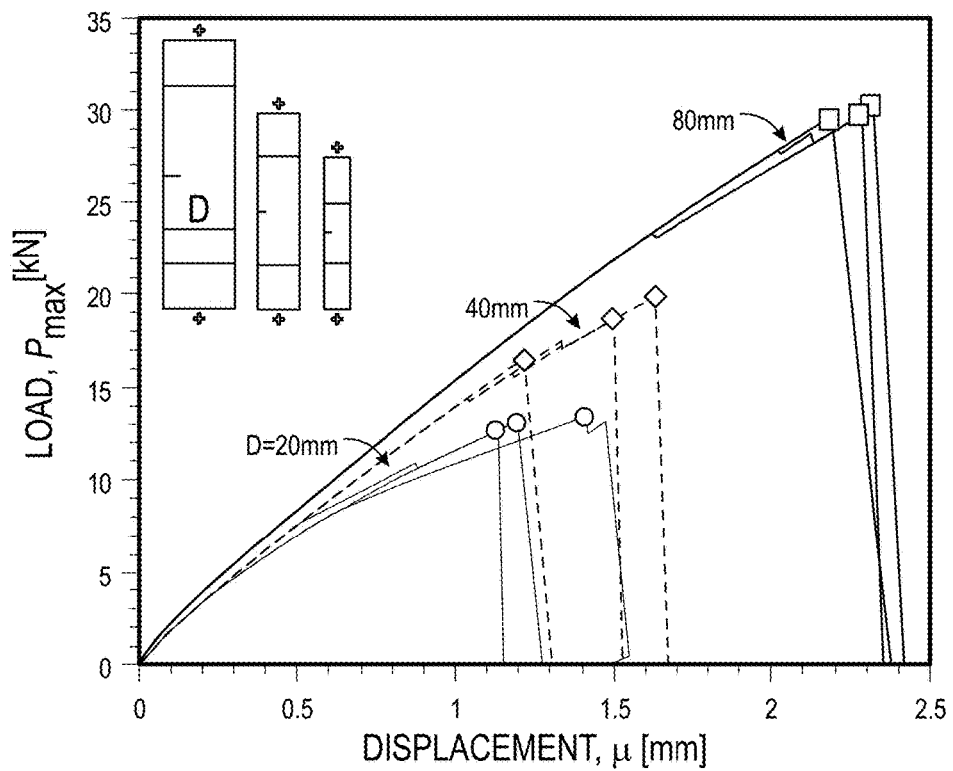
FIG. 11A depicts a) typical load-displacement curves of $[0°]_8$ geometrically-scaled SENT specimens of various sizes, showing decreasing nonlinearity at increasing specimen size; typical failure patterns of SENT specimens for width D=20 mm, D=40 mm, and D=80 mm.
Figure 11B:
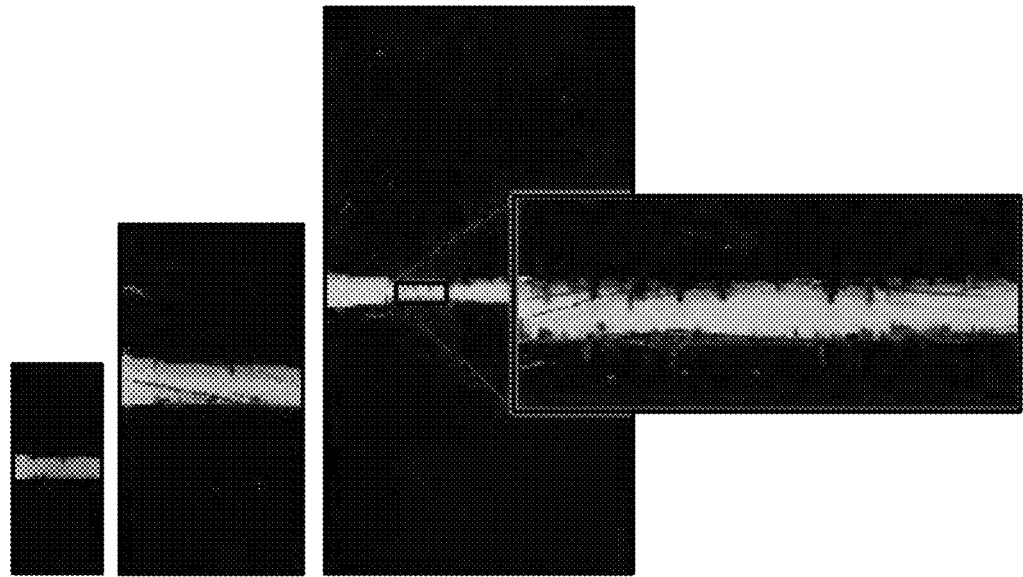
FIG. 11B is the magnification of the fracture surface for the large specimen showing extensive tow failure and pull-out.
Figure 12:
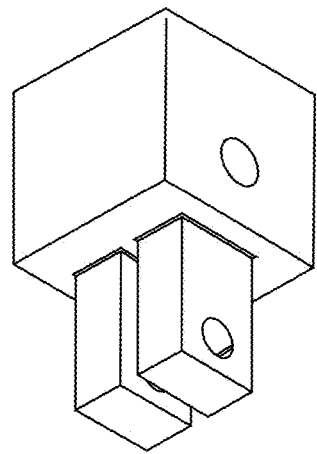
FIG. 12 shows an isometric view of a grip designed according to the present application.

The top surface of all the SENT specimens investigated was treated to allow Digital Image Correlation (DIC) analysis. A thin layer of white paint was deposited on a D×D area embedding the crack. Then, black speckles of average size 0.01 mm were spray-painted on the surface after drying.
Testing The Compact Tension (CT) test set-up is shown in FIG. 3. A universal testing machine (of MTS) was used to load the CT specimens at the rate of 1 mm/min. Tensile loading was applied through 20 mm diameter pins inserted through the holes shown in FIG. 1a. An extensometer was attached to the specimens to measure the pin opening displacement (POD). The load cell signal and the extensometer signal were output and recorded.
Size Effect Tests on Single Edge-Notched Tension (SENT) Specimens After the completion of the experiments, the load and displacement data were analyzed. FIG. 11 shows, for the various sizes, the typical load-displacement plots reported. For the largest specimen size, these curves are almost linear up to failure, which is an indication of pronounced brittle behavior.

Right after reaching the peak load, the specimens used for size effect became unstable for all the sizes and failed dynamically. This was no problem since the size effect analysis does not require postpeak (note that stiff grips cannot stabilize these specimens because the specimen itself is too soft and stores too much energy). The failed specimens showed microcracks within the layers, and tow breakage or pull-out. Delamination between the layers occurred before the peak load.

Note that that, according to strength-based criteria (e.g., Tsai and Wu [1]), the nominal strength would not depend on the structure size. However, Table 3 does show a significant decrease of σN with an increasing characteristic size of the specimen, which proves the strength based failure criteria to be incorrect.

From the size effect results, the initial fracture energy was obtained as G$_f$=73.7 N/mm.
Compact Tension Test Results FIG. 9 gives the load vs. pin opening displacement (POD) curves of all the tested specimens. For woven composite specimens, it can be seen that, the load vs. POD curves are approximately linear up to the first load drop. After that, the crack progresses in a series of small jumps which cause further load drops.

Figure 9A:
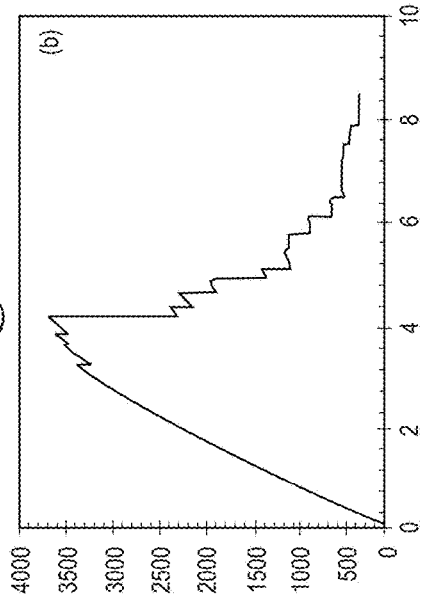
FIGS. 9A, 9B, 9C and 9D are examples of typical stable load-displacement curves obtained with grips designed in accordance with the present application for carbon fiber woven composites (a) and (b) and for glass fiber textile composites (c) and (d), respectively.
Figure 9B:
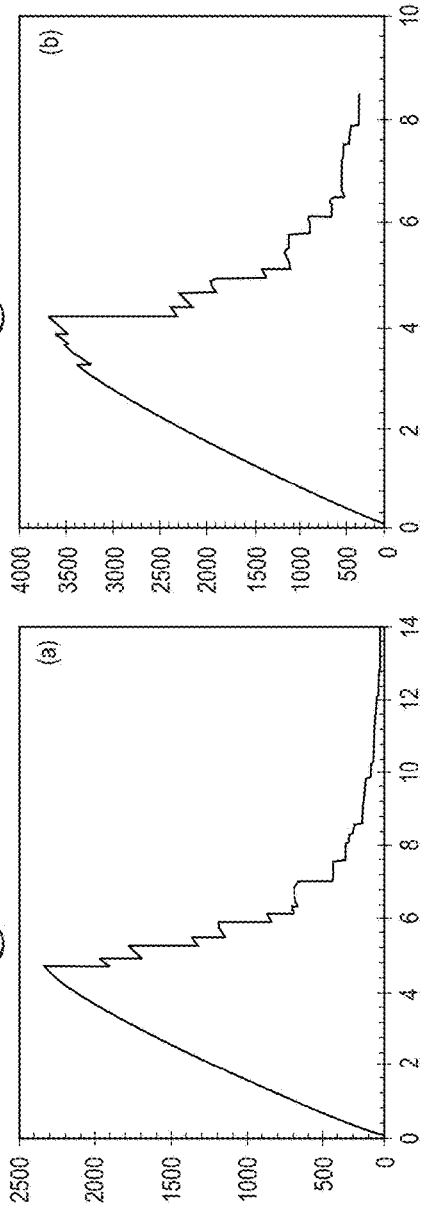
Figure 9C:
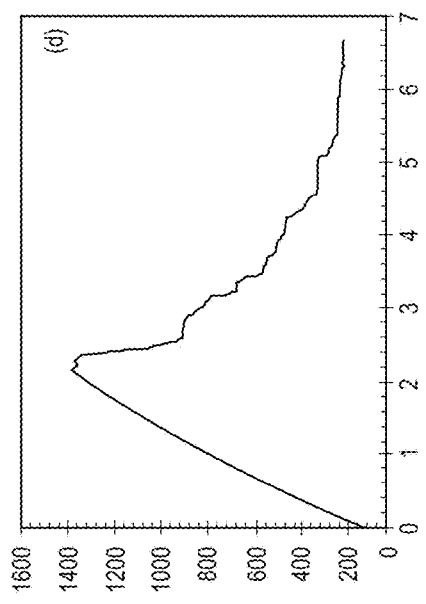
Figure 9D:
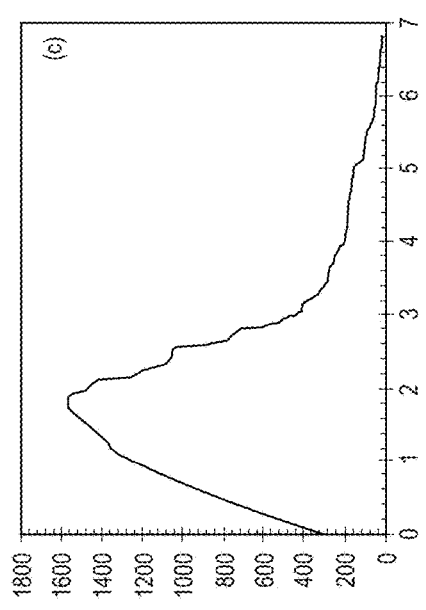

In contrast, the FRP specimens showed a large degree of non-linearity in the load vs. POD curves. FIGS. 9a,b and 9c,d show failure modes typical of woven composites and FRP composite specimens. The failure of woven composite is characterized by development of fiber breakage along the center line of the specimen toward the back. A small amount of splitting can be observed on either side of the fiber breaks, which caused flaking of the paint for the Digital Image Correlation (DIC).

From the load vs. POD curves (FIG. 9), the fracture energy of the composites can be estimated as [7]:

$$G_f = \frac{W}{bl_t} \tag{32}$$

where G$_f$=fracture energy, W=area under the load displacement curve, b=thickness of the specimen and l$_t$=ligament length. The calculated fracture energies for woven composites are 76.34 N/mm and 79.74 N/mm for specimen 1 and specimen 2 respectively. These results are very close to the fracture energy calculated from the size effect using the size effect test (since the size effect method gives the fracture energy corresponding only to the area under the initial tangent to the cohesive stress-displacement law, it appears that this law should not have a long tail of small slope). The fracture energies of FRP composites deduced from the size effect were 14.16 N/mm and 13.09 N/mm for specimens 1 and 2, respectively.

Example

Designing a grip according to the present application may be done based on calculated stiffness. The basic design of a grip includes two parallel steel legs extending from a base to form a generally U-shaped clevis, with the legs defining a slot for receiving the test specimen. A pin is used to secure the test specimen to the parallel legs, and the entire grip is secured to the load frame by either a threaded shaft or a threaded bore.

The design process is iterative and includes the following steps:
(1) The stiffness of the grip is calculated and entered into the proposed stability criterion (e.g., equation 5) to check if stable testing is enabled.
(2) If the stability criteria are not satisfied, the design is improved and step (1) repeated.
(3) Step (2) is repeated until the stability criteria are satisfied.

Figure 13A:
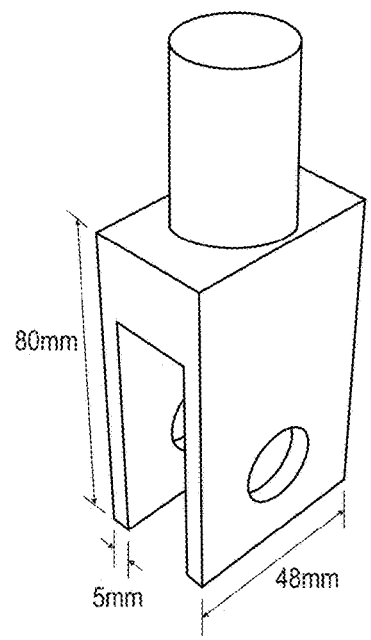
FIGS. 13A, 13B, and 13C comprise perspective views of grips designed using iteratively the method described herein to provide an a) an initial design, b) a second design, and c) a final design (corresponding to the grip shown in FIG. 12), respectively.
Figure 13B:
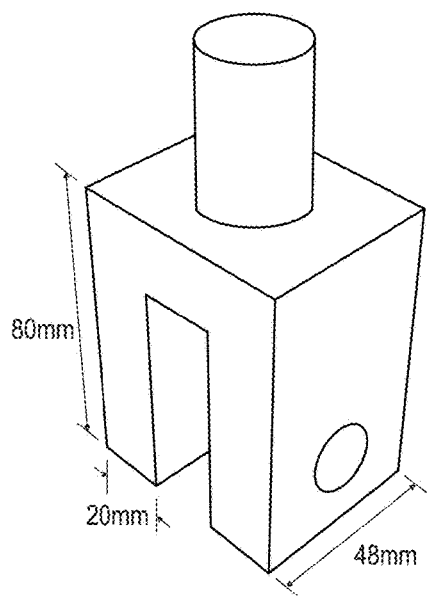
Figure 13C:
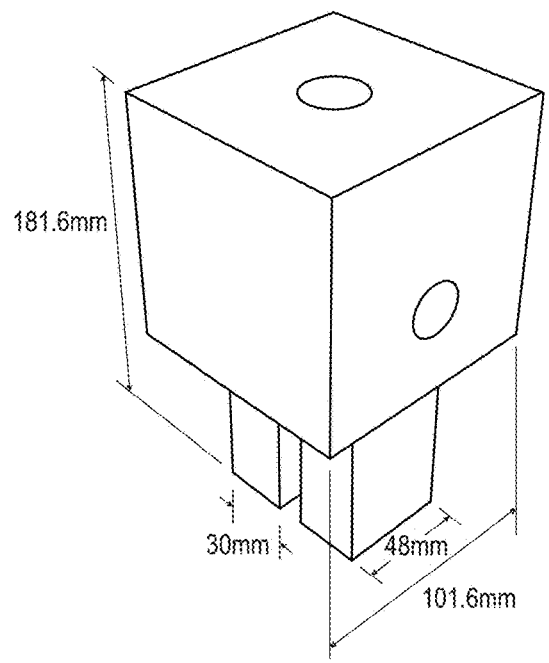

With reference to FIGS. 13a), 13b) and 13c), three grips are shown that demonstrate an example of the designing process. From design 13a) to 13c), the grips are made to be more massive, particularly in the base, and an increase in the calculated grip stiffness is observed. Only the final design, FIG. 13c), satisfies the stability criteria.

The procedure for calculating the stiffness of the grip requires first creating a 3D CAE model of the grip using a commercially-available CAD software (such as the Autodesk Inventor design application). The model is then imported into a finite element program for mechanical analysis (such as that available from Abaqus Inc.), and material properties are assigned and boundary conditions applied to simulate the loading conditions of an actual test. The stiffness of the designed grip, K, is calculated as load, F, divided by the load-point displacement, d, obtained from the post-processing results (i.e., K=F/d).

REFERENCES

[1] Tsai S. W., Wu E. M. A General Theory of Strength for Anisotropic Materials J Compos Mater 1972; 5:5880
[2] Hinton, M. J., and Soden, P. D. (1998). "Predicting failure in composite laminates: the background to the exercise." *Compos. Sci. Technol. J.* 58, 1001-1010.
[3] Soden, P. D. Hinton, M. J., Kaddour, A. S. (1998). "A comparison of the predictive capabilities of current failure theories for composite laminates" *Compos. Sci. Technol. J.* 58 (special issue), 1225-1254.
[4] Hinton, M. J., Kaddour, A. S., and Soden, P. D. (2002). "A comparison of the predictive capabilities of current failure theories for composite laminates, judged against experimental evidence" *Compos. Sci. Technol. J.* 62 (special issue), 1725-1797.
[5] Bažant, Z. P. (1984). "Size effect in blunt fracture: Concrete, rock, metal." *J. of Engrg. Mechanics*, ASCE, 110 (4), 518-535.
[6] Bažant, Z. P., and Cedolin, L. 1991, *Stability of Structures: Elastic, Inelastic, Fracture and Damage Theories*, Oxford University Press, New York (also 2nd. ed. Dover Pub. 2003, 3rd ed. World Scientific 2010).
[7] Bažant Z. P., Planas, J., 1998. "Fracture and Size Effect in Concrete and Other Quasibrittle Material." *CRC Press*, Boca Raton and London.
[8] Bažant Z. P., Daniel I. M., Li Z., 1996. "Size Effect and Fracture Characteristics of Composite Laminates" *J. Eng. Mater. Technol.* 118 (3): 317324.
[9] Green B. G., Wisnom M. R., Hallet S. R., 2007 "An experimental investigation into the tensile strength scaling of notched composites." *Composites—Part A* 38, 867-78.
[10] Bažant Z. P. (1976) Instability, ductility and size effect in strain-softening concrete. J Eng Mech Div ASCE 1976; 102:331-44.
[11] ASTMD5528 Standard Test Method for Mode I Interlaminar Fracture Tough-ness of Unidirectional Fiber-Reinforced Polymer Matrix Composites 2007.
[12] Bažant Z. P. 1999. "Size effect on structural strength: a review" *Archive of Applied Mechanics* 69: 703725.
[13] Bažant Z. P., Kim J-J H., Daniel I. M., Becq-Giraudon E., Zi G. 1999. "Size effect on compression strength of fiber composites failing by kink band propagation" *Int J Fracture* 95: 103141.
[14] Bažant Z. P., Zhou Y., Novak D., Daniel I. M. 2004. "Size Effect on Flexural Strength of Fiber-Composite Laminates" *J. Eng. Mater. Technol* 126: 2937.
[15] Salviato M., Kirane K., Ashari S., Bažant Z. P., Cusatis G. 2016. "Experimental and Numerical Investigation of Intra-Laminar Energy Dissipation and Size Effect in Two-Dimensional Textile Composites", arXiv:1605.06174
[16] Salviato, M. Kirane, K., Ashari, S. E., Bažant, Z. P., and Cusatis, G. (2016). "Experimental and Numerical Investigation of Intra-Laminar Energy Dissipation and Size Effect in Two-Dimensional Textile Composites." *Composites Science and Technology*, in press.
[17] Bažant, Z. P., Chau, V. T., Cusatis, G., and Salviato, M. (2016). "Direct Testing of Gradual Postpeak Softening of Notched Specimens of Fiber Composites Stabilized by Enhanced Stiffness and Mass," arXiv:1607.00741 (4 Jul. 2016).
[18] Rüsch, H. and Hilsdorf, H. (1963). "Deformation characteristics of concrete under axial tension". Voruntersuchungen Bericht (preliminary report) No. 44, Munich, May 1963.
[19] Hughes, B. P., and Chapman, G. P. (1966). "The complete stress-strain curve for concrete in direct tension." RILEM Bulletin (Paris) 30, 95-97.
[20] Evans, R. H., and Marathe, M. S. (1968). "Microcracking and stress-strain curves in concrete for tension." *Materials and Structures* Vol. 1, 61-64.
[21] Heilmann, H. G., Hilsdorf, H., and Finsterwalder, K. (1969). "Festigkeit und Verformung von Beton unter Zugspannungen." Deutscher Ausschu s für Stahlabeton, Heft 203.
[22] Wawersik W. R. and Fairhurst, C. (1970) A study of brittle rock fracture in laboratory compression experiments. Int. J. Rock Mech. Min. Sci. Vol 7, No. 5, PP. 561-575.
[23] Hudson, J. A., Brown E. T. and Fairhurst. C (1971) Optimizing the control of rock failure in servo-controlled laboratory tests. Rock Mech. Vol 3. pp 217-224.
[24] Fairhurst, C., private communication on Jun. 23, 2016 to Z. P. Bazant of the photo of the first MTS stiff machine built in 1968 in collaboration with Fairhurt and Wawerskik.
[25] ASTMD5045 Standard Test Methods for Plane-Strain Fracture Toughness and Strain Energy Release Rate of Plastic Materials 1999.
[26] Bažant Z. P., Tabbara M. R. 1992 Bifurcation and Stability of Structures with Interacting Propagating Cracks. Int. J. of Fracture; 53:273-289.

The invention claimed is:
1. A system comprising:
a linear fracture testing machine configured to test a specimen, wherein the linear fracture testing machine has a frame stiffness $K_m$ and the specimen has an incremental stiffness $K_s$;
grips configured to secure to the linear fracture testing machine and secure the specimen, wherein the grips are configured to have a stiffness $K_g$ to enable stable postpeak measurements of the specimen under a Crack Mouth Opening Displacement (CMOD) control, wherein a combined stiffness of the linear fracture testing machine and the grips $K_{mg}=1/(1/K_m+1/K_g)$, and a total stiffness of the specimen, the linear fracture testing machine, and the grips $K_t=1/(1/K_m+1/K_g)+K_s>-0-$;
an extensometer configured to measure the Crack Mouth Opening Displacement (CMOD) of the specimen; and
a closed-loop servo control system coupled to the linear fracture testing machine, the grips, and the extensometer, to control testing of the specimen based on a Proportional-Integrative-Differential (PID) signal.

2. The system of claim 1, wherein the grips are configured to enhance controllability of the stable postpeak measurements based on a mass and the stiffness $K_g$ of the grips.

3. The system of claim 1, wherein the specimen is a quasi-brittle material and has a negative incremental stiffness.

4. The system of claim 1, wherein $K_m$ is about 200 MN/m, $K_s$ is about −0.830 MN/m, and $K_g$ is about 192.4 MN/m, and the mass of the grips is about 9.419 kg.

5. The system of claim 1, wherein the grips have a stiffness $K_g=1/(K_s/K_t-1/K_m+1K_t)>-0-$.

6. The system of claim 5, wherein $K_m$ is about 200 MN/m, $K_s$ is about −0.830 MN/m, and $K_g$ is about 192.4 MN/m, and the mass of the grips is about 9.419 kg.

7. Grips, configured to:
secure to a linear fracture testing machine;
secure a specimen that is a quasi-brittle material and has a negative incremental stiffness;
and
have a stiffness $K_g$ to enable stable postpeak measurements of the specimen under a Crack Mouth Opening Displacement (CMOD) control, wherein a combined stiffness of the linear fracture testing machine and the grips $K_{mg}=1/(1/K_m+1/K_g)$, and a total stiffness of the specimen, the linear fracture testing machine, and the grips $K_t=1/(1/K_m+1/K_g)+K_s>-0-$, wherein each of the grips comprises a base and first and second parallel legs extending from the base defining a slot for receiving the specimen, and each of the grips is massive in the base to enhance controllability of the stable postpeak measurements based on a mass of the grips.

8. The grips of claim 7, wherein each of the first and second parallel legs has an aperture therein for receiving a pin by which the specimen is secured to the grip.

9. The grips of claim 7, wherein $K_m$ is about 200 MN/m, $K_s$ is about −0.830MN/m, and $K_g$ is about 192.4 MN/m, and the mass of the grips is about 9.419 kg.

10. The grips of claim 7, wherein the grips have a stiffness $K_g=1/(K_s/K_t-1/K_m+1/K_t)>-0-$.

11. The grips of claim 10, wherein Km is about 200 MN/m, $K_s$ is about −0.830 MN/m, and $K_g$ is about 192.4 MN/m, and the mass of the grips is about 9.419 kg.

12. A method of manufacturing grips for a linear fracture testing machine, wherein the grips are manufactured to have a mass and a stiffness to enable stable postpeak measurements of a specimen under a Crack Mouth Opening Displacement (CMOD) control, the specimen has a negative incremental stiffness, and the method comprises:
inputting variables comprising:
an incremental stiffness ($K_s<0$) of the specimen;
a stiffness of the linear fracture testing machine ($K_m>0$);
a mass of the specimen;
a mass of the linear fracture testing machine;
a time delay of the linear fracture testing machine; and
Proportional-Integrative-Differential (PID) parameters for the combination of the linear fracture testing machine, the grips, and the specimen;
determining the mass and the stiffness of the grips by solving $$\begin{bmatrix} -\lambda & 1 & 0 & 0 & 0 \\ -\frac{1}{m}\left(K_g+\frac{\partial K_s}{\partial x_1}\right) & -\lambda & \frac{K_g}{m} & 0 & 0 \\ 0 & 0 & -\lambda & 1 & 0 \\ R_1 & -\frac{\beta K_M}{M} & R_2 & -\frac{K_M \tau}{M} & -\frac{K_m \gamma}{M}-\lambda \\ 1 & 0 & 0 & 0 & -\lambda \end{bmatrix} \quad (28)$$

$$R_1 = \frac{K_g - \alpha K_M}{M} + \frac{K_M \tau}{M}\left[\gamma + \beta\frac{\partial K_s/\partial x_1 + K_g}{m}\right] \quad (29)$$

$$R_2 = -\frac{K_M + K_g}{M} + \frac{\beta \tau K_g K_M}{mM} \quad (30)$$

so that the eigenvalues are negative; and
manufacturing the grips having the determined mass and stiffness, wherein each of the grips comprises:
a base having one of a threaded shaft or a threaded bore for securing the grip to the linear fracture testing machine; and
first and second parallel legs extending from the base of each grip.

13. The method of claim 12, wherein the determined stiffness of the grips $K_g=1/(K_s/K_t-1/K_m+1/K_t)>-0-$, wherein
$K_s$, is an incremental stiffness of the specimen;
$K_t$ is a total stiffness of the specimen, the linear fracture testing machine, and the grips; and
$K_m$ is the stiffness of the linear fracture testing machine.

14. The method of claim 12, wherein each of the manufactured grips is massive in the base.

15. The method of claim 12, wherein each leg of the grips comprises an aperture therein for receiving a pin by which the specimen is secured to the grips.

* * * * *